United States Patent
Ritter et al.

(10) Patent No.: US 8,274,037 B2
(45) Date of Patent: Sep. 25, 2012

(54) AUTOMATIC CALIBRATION TECHNIQUE FOR TIME OF FLIGHT (TOF) TRANSCEIVERS

(75) Inventors: David W. Ritter, San Jose, CA (US); Carl Warren Craddock, San Francisco, CA (US); Philip Golden, Menlo Park, CA (US)

(73) Assignee: Intersil Americas Inc., Milpitas, CA (US)

( * ) Notice: Subject to any disclaimer, the term of this patent is extended or adjusted under 35 U.S.C. 154(b) by 138 days.

(21) Appl. No.: 13/013,173

(22) Filed: Jan. 25, 2011

(65) Prior Publication Data

US 2011/0181892 A1 Jul. 28, 2011

Related U.S. Application Data

(60) Provisional application No. 61/298,895, filed on Jan. 27, 2010.

(51) Int. Cl.
*H01L 31/00* (2006.01)
*H01J 40/14* (2006.01)

(52) U.S. Cl. .............. 250/214.1; 250/241 A; 250/214 R; 250/338.1; 324/76.77

(58) Field of Classification Search .............. 356/3, 614, 356/213, 228, 229; 250/214.1, 214 A, 241 R, 250/338.1; 324/76.77
See application file for complete search history.

(56) References Cited

U.S. PATENT DOCUMENTS

| | | | |
|---|---|---|---|
| 3,996,590 A | 12/1976 | Hammack | |
| 4,458,212 A | 7/1984 | Brehmer et al. | |
| 4,542,475 A | 9/1985 | Acampora | |
| 4,551,710 A | 11/1985 | Troup et al. | |
| 4,648,364 A | 3/1987 | Wills | |
| 4,942,561 A | 7/1990 | Ohishi et al. | |
| 5,055,671 A | 10/1991 | Jones | |
| 5,469,748 A * | 11/1995 | Kalotay | ................... 73/861.356 |
| 5,563,701 A | 10/1996 | Cho | |
| 5,593,430 A | 1/1997 | Renger | |

(Continued)

FOREIGN PATENT DOCUMENTS

WO 198704034 A1 7/1987

(Continued)

OTHER PUBLICATIONS

Silicon Labs Si1120, "QuickSense™ Si1120 Proximity and Ambient Light Sensor ICs", http://www.silabs.com/products/sensors/infraredsensors/Pages/Si1120.aspx [retrieved Dec. 28, 2010].

(Continued)

*Primary Examiner* — Sang Nguyen

(74) *Attorney, Agent, or Firm* — Fliesler Meyer LLP

(57) ABSTRACT

A system and method for automatically calibrating a Time-of-Flight (TOF) transceiver system for proximity/motion detection, is provided. Moreover, the system comprises a component that senses a signal (e.g., current or voltage) at an light emitting diode (LED), an attenuator, a signal injector at a sensor and a switching circuit that toggles between a normal mode (e.g., when signal from the sensor is input to the sensor front end) and a calibration mode (e.g., when signal from the attenuator is input to the sensor front end). During the calibration mode, the sensor front end identifies the phase delay error within the signal path, including board and/or package parasitic, and accounts for the phase delay error during proximity/motion detection in the normal mode.

20 Claims, 8 Drawing Sheets

U.S. PATENT DOCUMENTS

| | | | | |
|---|---|---|---|---|
| 5,742,379 | A | * | 4/1998 | Reifer .................. 356/5.07 |
| 5,828,899 | A | | 10/1998 | Richard et al. |
| 5,892,540 | A | | 4/1999 | Kozlowski et al. |
| 6,111,256 | A | | 8/2000 | Shpater |
| 6,392,539 | B1 | | 5/2002 | Kanasugi |
| 6,462,726 | B1 | | 10/2002 | Hamada et al. |
| 6,744,248 | B2 | | 6/2004 | Buchhold et al. |
| 6,753,950 | B2 | | 6/2004 | Morcom |
| 6,803,555 | B1 | | 10/2004 | Parrish et al. |
| 6,819,782 | B1 | | 11/2004 | Imagawa et al. |
| 6,836,212 | B2 | | 12/2004 | Sawinski |
| 6,888,938 | B2 | | 5/2005 | Cui et al. |
| 7,212,655 | B2 | | 5/2007 | Tumey et al. |
| 7,486,386 | B1 | | 2/2009 | Holcombe et al. |
| 7,532,870 | B2 | | 5/2009 | Ling |
| 7,616,032 | B2 | | 11/2009 | Jang |
| 7,619,293 | B2 | | 11/2009 | Hasegawa |
| 7,620,202 | B2 | | 11/2009 | Fujimura et al. |
| 7,735,037 | B2 | * | 6/2010 | Tell ........................ 716/113 |
| 2002/0097743 | A1 | | 7/2002 | Baydar et al. |
| 2003/0234341 | A1 | | 12/2003 | Osborn |
| 2006/0120621 | A1 | | 6/2006 | Larkin et al. |
| 2007/0013791 | A1 | | 1/2007 | Kinoshita et al. |
| 2007/0121095 | A1 | | 5/2007 | Lewis et al. |
| 2008/0119716 | A1 | | 5/2008 | Boric-Lubecke et al. |
| 2008/0205820 | A1 | | 8/2008 | Zheng et al. |
| 2008/0266128 | A1 | | 10/2008 | Leone et al. |
| 2009/0006730 | A1 | | 1/2009 | Gara et al. |
| 2009/0027529 | A1 | | 1/2009 | Jung et al. |
| 2009/0283699 | A1 | * | 11/2009 | Baltz et al. ............. 250/459.1 |
| 2009/0295729 | A1 | | 12/2009 | Kuo et al. |
| 2010/0066442 | A1 | * | 3/2010 | Mu ........................... 327/553 |
| 2011/0180693 | A1 | * | 7/2011 | Ritter et al. ............. 250/214 A |
| 2011/0180709 | A1 | * | 7/2011 | Craddock et al. ......... 250/338.1 |

FOREIGN PATENT DOCUMENTS

WO       2009088662 A2       7/2009

OTHER PUBLICATIONS

Sharp Electronics Corporation, "GP2Y0A02YK0F Sales and Technical Information", http://www.sharpmeg.com/Page.aspx/americas/en/part/GP2Y0A02YK0F/ [retrieved Dec. 28, 2010].

Theodore D. Rees, "Long Range Proximity and/or Motion Detector With Ambient Light Detection Capabilities", U.S. Appl. No. 61/173,951, filed Apr. 29, 2009.

Capella Microsystems, Inc. "Proximity Sensor", http://www.capellamicro.com.tw/EN/products_list.php?mode=16 copyright 2009 [retrieved Mar. 14, 2011].

Capella Microsystems, Inc. "Ambient Light Sensor (ALS)", http://www.capellamicro.com.tw/EN/products_list.php?mode=14 copyright 2009 [retrieved Mar. 14, 2011].

OPTEK Technology Inc. "Long Distance Reflective Switch OPB720A and OPB720B Series", http://www.optekinc.com/datasheets/opb720a-06z.pdf, Issue F.1, Jan. 2008.

Intersil, "Low Power Ambient Light and Proximity Sensor with Intelligent Interrupt and Sleep Modes", ISL29028, FN6780.1, Mar. 2, 2010.

Silicon Labs Si1120, "Proximity/Ambient Light Sensor With PWM Output", Rev. 1.0 8/10 Copyright 2010 by Silicon Laboratories.

Nemecek et al., "Distance Measurement Sensor With PIN-Photodiode and Bridge Circuit", IEEE Sensors Journal, vol. 6, No. 2, pp. 391-397, Apr. 2006.

Gokturk et al, "A Time of Flight Depth Sensor—System Description, Issues and Solutions", 2004 Conference on Computer Vision and Pattern Recognition Workshop (CVPRW'04) vol. 3, Washington, D.C., USA, Jun. 27-Jul. 2, 2004.

Dongmyung Lee et al., "An 8.5Gb/s CMOSOEIC with On-chip Photodiode for Short Distance Optical Communications", 2010 IEEE International Solid-State Circuits Conference, Solid-State Circuits Conference Digest of Technical Papers (ISSCC), 2010 IEEE International, pp. 362-363, Feb. 7-11, 2010.

International Search Report and Written Opinion, mailing dated Mar. 25, 2011, for International Application No. PCT/US11/22644, 8 pages.

Ryan, et al., "A long-range, widefield-of-view, infrared eyeblink detector". Journal of Neuroscience Methods 152 (2006) 74-82, Apr. 2006, abstract: Fig 3, 4: pp. 79, col. 2.

International Search Report and Written Opinion, mailing date Mar. 21, 2011, for International Application No. PCT/US11/022646, 14 pages.

International Search Report and Written Opinion, mailing date Apr. 6, 2011, for International Application No. PCT/US2011/022647, 17 pages.

International Search Report and Written Opinion, mailing date Mar. 28, 2011, for International Application No. PCT/US2011/022649, 13 pages.

International Search Report and Written Opinion, mailing date Mar. 28, 2011, for International Application No. PCT/US2011/022650, 10 pages.

International Search Report and Written Opinion, mailing date Mar. 25, 2011, for International Application No. PCT/US2011/022651, 14 pages.

* cited by examiner

AUTOMATIC CALIBRATION TECHNIQUE FOR TIME OF FLIGHT (TOF) TRANSCEIVERS

CROSS REFERENCE TO RELATED APPLICATIONS

This application claims priority to U.S. Provisional Patent Application Ser. No. 61/298,895, filed on Jan. 27, 2010, and entitled "ARCHITECTURE FOR A REFLECTION BASED LONG RANGE PROXIMITY AND MOTION DETECTOR HAVING AN INTEGRATED AMBIENT LIGHT SENSOR," the entirety of which is incorporated by reference herein. Further, this application is related to U.S. Patent application Ser. No. 12/979,726, filed on Dec. 28, 2010, entitled "DISTANCE SENSING BY IQ DOMAIN DIFFERENTIATION OF TIME OF FLIGHT (TOF) MEASUREMENTS," U.S. Patent application Ser. No. 13/013,146, filed on Jan. 25, 2011, entitled "DIRECT CURRENT (DC) CORRECTION CIRCUIT FOR A TIME OF FLIGHT (TOF) PHOTODIODE FRONT END", U.S. Patent application Ser. No. 13/013,199, filed on Jan. 25, 2011, entitled "PHOTODIODE FRONT END WITH IMPROVED POWER SUPPLY REJECTION RATIO (PSRR)," U.S. Patent application Ser. No. 13,013,640, filed on Jan. 25, 2011, entitled "SERIAL-CHAINING PROXIMITY SENSORS FOR GESTURE RECOGNITION", and U.S. Patent application Ser. No. 13/013,676, filed on Jan. 25, 2011, entitled "GESTURE RECOGNITION WITH PRINCIPAL COMPONENT ANALYSIS." The entireties of each of the foregoing applications are incorporated herein by reference.

DETAILED DESCRIPTION

Figure 1:
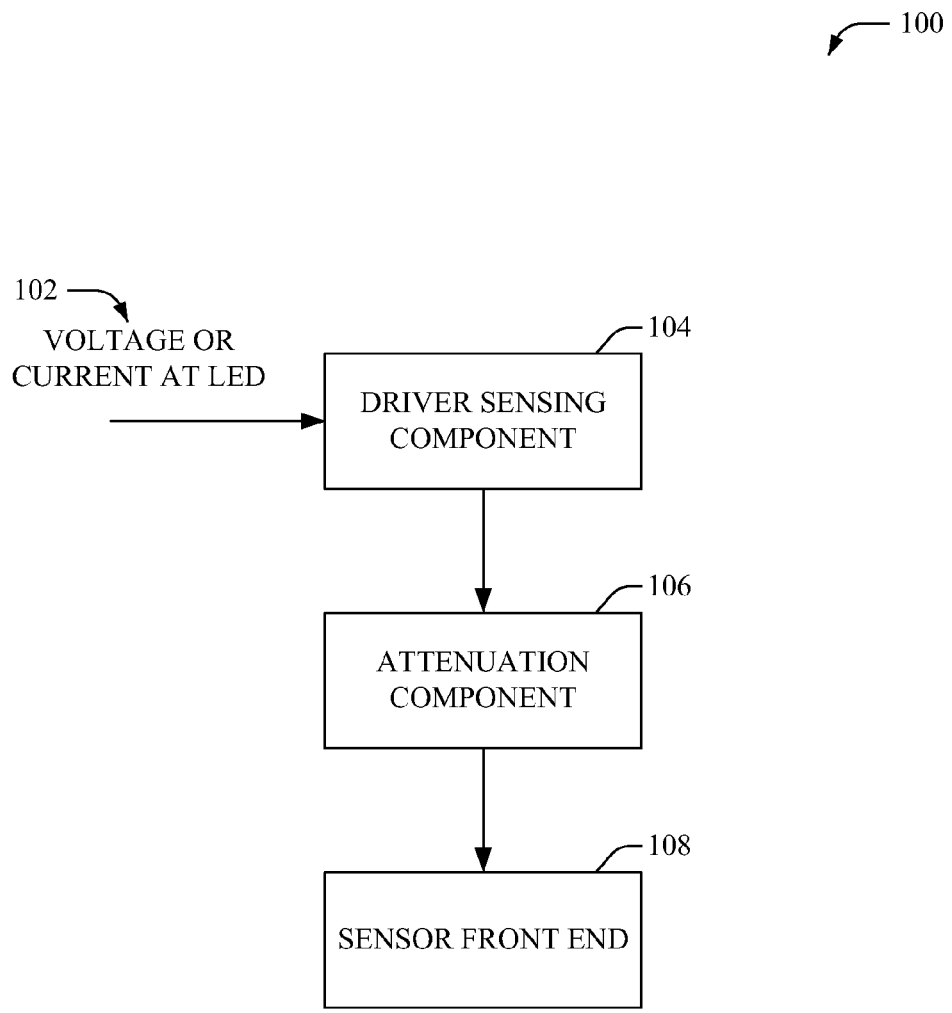
FIG. 1 illustrates an exemplary system for automatically calibrating a long range proximity detector.

A category of monolithic devices is emerging that allows electronic products to sense their environment. These include diverse devices, such as, accelerometers, monolithic gyroscopes, light sensors and imagers. In particular, light sensors are one of the simplest and cheapest, allowing their inclusion in multitudes of consumer products, for example, nightlights, cameras, cell phones, laptops etc. Typically, light sensors can be employed in a wide variety of applications related to proximity sensing, such as, but not limited to, detecting the presence and/or distance of a user to the product for the purpose of controlling power, displays, or other interface options.

Infrared (IR) proximity detectors utilize IR light to detect objects within the sense area of the IR sensor. Moreover, IR light is transmitted by an IR Light emitting diode (LED) emitter, which reflects off of objects in the surrounding area and the reflections are sensed by a detector. Moreover, the detector can be a diode, e.g., a PIN diode, and/or any other type of apparatus that converts IR light into an electric signal. The sensed signal is analyzed to determine whether an object is present in the sense area. Typically, time of flight (TOF) systems transmit a pulse of IR light and detect whether the pulse is returned back at the PIN diode. Moreover, if an object is present within the sense area, the pulse of IR light is reflected back from the object and the distance of the object is calculated based on the time delay to receive the reflected pulse. However, an additional time and/or phase delay is added by various components of the TOF system, such as, a light emitting diode (LED), LED driver, sensor front end, etc. This time and/or phase delay can create significant errors in distance measurements. Thus, to compensate for these errors, the conventional systems can be manually calibrated by placing a known object at a known distance from the sensor. However, performing this manual calibration is a tedious and time consuming process and can lead to customer dissatisfaction. In addition, traditional systems fail to account for package parasitics and/or board parasitics.

The systems and methods disclosed herein provide an automatic calibration scheme for an active long-range distance sensor, employed for proximity and/or motion detection. Typically, "proximity detection" can be defined as measuring a "distance" from the sensor to an object, and "motion detection" can be defined as measuring "presence" in front of the sensor. Moreover, the range of the disclosed distance sensor can be from 1 centimeter to 30 meters. In one aspect, a signal is modulated at a high frequency, for example 1 MHz-50 MHz, and emitted by an LED (e.g., Infrared (IR) LED). The automatic calibration system disclosed herein utilizes the voltage or current at the LED as a sensing variable and compensates for errors in the signal path, including, but not limited to, package and board parasitics, during the calibration. It can be appreciated that although the subject specification is described with respect to IR wavelengths, the systems and methods disclosed herein can utilize most any wavelength. As an example, the subject system and/or methodology can be employed for acoustical proximity detection and/or ultrasonic range finding applications. Further, although the subject specification illustrates and describes light/optical sensors (e.g., photodiodes), it can be appreciated that most any circuit element that converts a physical input into an electrical signal.

The subject matter is described with reference to the drawings, wherein like reference numerals are used to refer to like elements throughout. In the following description, for purposes of explanation, numerous specific details are set forth in order to provide a thorough understanding of the subject innovation. It may be evident, however, that the subject matter may be practiced without these specific details. In other instances, well-known structures and devices are shown in block diagram form in order to facilitate describing the subject innovation. Of course, those skilled in the art will recognize that many modifications may be made to this configuration without departing from the scope or spirit of the claimed subject matter.

Moreover, the word "exemplary" is used herein to mean serving as an example, instance, or illustration. Any aspect or design described herein as "exemplary" is not necessarily to be construed as preferred or advantageous over other aspects or designs. Rather, use of the word "exemplary" is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form. In addition, the word "coupled" is used herein to mean direct or indirect electrical or mechanical coupling. Further, the terms "sense area," "vision field," "optical field," and similar terminology are utilized interchangeably in the subject application, unless context warrants particular distinction(s) among the terms.

Referring to FIG. 1, there illustrated is an example system 100 for automatically calibrating a long range proximity detector, in accordance with an aspect of the subject disclosure. In general, system 100 can be employed in most any light sensing application. For example, a laptop or personal computer can power-up (e.g., from hibernation, stand-by, etc.) on detecting that a user has entered a room and/or power-down (e.g., hibernate, sleep, switch off, etc.) on detecting that the user has left the room. In another example, a cell phone or personal digital assistant (PDA) can switch off a display (to conserve battery life) when detected that the phone/PDA is held at the user's ear. Moreover, the sensor output can be utilized by various systems, such as, but not limited to, power saving systems (e.g., modifies display brightness or keypad backlighting to conserve battery life), security systems (e.g., locks workstation or disables screen when user departs), media systems (e.g., provides an interactive experience by changing music/media modes), etc. In yet another example, system 100 can be employed in the automotive industry, e.g., touch screen in the central display, safety system, in-car Bluetooth system and/or driver detection system. Further, system 100 can be utilized in touch-less switches (e.g., sanitary equipment, touch-less light fixtures, product dispensing system). Furthermore, automated teller machines (ATMs), vending machines, printers, copiers, scanners, etc. can include system 100.

In one embodiment, system 100 facilitates calibration for distance sensing in a TOF transceiver, according to an aspect of the subject specification. Typically, an emitter (e.g. light emitting diode (LED)) and a sensor (e.g., photodiode) are utilized in TOF proximity/motion detection, wherein a signal emitted by the emitter, reflects off of object(s) in the vision field and is received by the sensor. Moreover, a phase or time delay relating to the signal received at the sensor is analyzed to identify proximity and/or motion of the object(s). In one aspect, system 100 facilitates calibration of the TOF transceiver, such that, errors introduced in the signal path can be reduced. Moreover, system 100 includes a driver sensing component 104, an attenuation component 106 and a sensor front end 108.

The driver sensing component 104 employs voltage or current at the LED (102) as a sensing variable. As an example, an integrated circuit (IC) chip (shown in FIG. 5), housing the LED driver and/or LED, can include an additional "sense" pin(s). Moreover, the driver sensing component 104, attenuation component 106 and sensor front end 108 can be external to the IC. In this example, the driver sensing component 104 can include an external resistor that is connected to the sense pin(s) to measure voltage or current at the LED. This allows package and board parasitics to be included in the calibration. In another example, the sensing component 104, attenuation component 106 and sensor front end 108 can be included within the IC itself.

The driver sensed signal is then attenuated by attenuation component 106 that reduces the amplitude or power of the driver sensed signal without changing its phase information. As an example, attenuation component 106 can be a passive device comprising simplistic voltage divider network(s). The attenuation component can be a V/I attenuator that inputs voltage and outputs attenuated current or an I/I attenuator that inputs current and outputs attenuated current. The attenuated signal is then provided to the sensor front end 108, via a switch (shown in detail infra, with respect to system 300 and 400). Based on the attenuated signal, the sensor front end 108 can identify and compensate for phase errors in the signal path, including, but not limited to analog front end, digital signal processing (DSP), LED driver, board and package parasitics. In one example, the sensor front end 108 can include amplifier(s), filter(s), demodulator, most any analog and/or digital signal processing circuits, and/or most any circuits that conform, the signal generated by the sensor to a specification, a back end can use. It can be appreciated that multiple ICs or apparatus can be employed to implement system 100.

Figure 2:
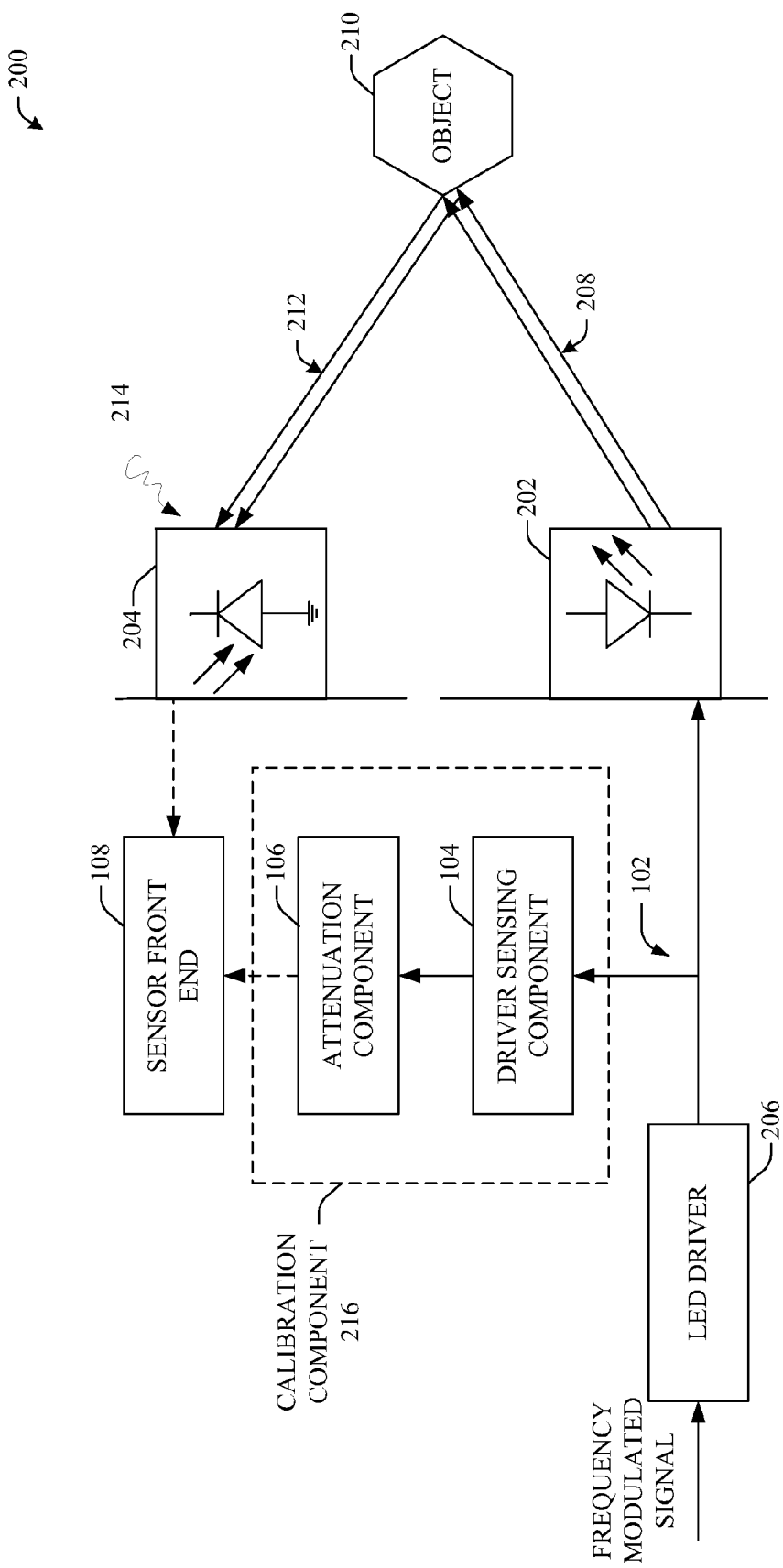
FIG. 2 illustrates an exemplary system for accurate proximity and/or motion sensing, according to an aspect of the subject disclosure.

Referring to FIG. 2, there illustrated is an example system 200 for accurate proximity and/or motion sensing, according to an aspect of the subject disclosure. Typically, system 200 employs an IR LED 202 and an IR sensor 204 (e.g., PIN photodiode). For example, the system 200 can employ a high frequency (e.g., 5 MHz) modulated LED 202 and a tuned PIN detector 204 to optimize the detection range. Moreover, an LED driver 206 can be employed to supply regulated power to LED 202. In one aspect, the LED driver 206 provides a frequency modulated signal (e.g., 1 MHz-50 MHz) as input to the IR LED 202. Typically, a local oscillator (not shown) synchronous with the LED driver 206 can also be utilized for synchronous detection (e.g., by the sensor front end 108). As an example, the IR LED 202 has a typical peak wavelength that matches the proximity sensor spectrum, a narrow viewing angle with higher radiant intensity that can facilitate concentrating the energy that is ideal for proximity sensing. It can be appreciated that most any IR LED (or array) can be employed based on the factors, such as, but not limited to, view-angle, mechanic height, footprint, radiant intensity, current consumption, etc. Further, the IR LED 202 can emit the modulated IR signal 208 to the object 210, and the IR sensor 204 can receive a portion 212 of the transmitted signal, which is reflected back from the surface of object 210. The object 210 can be most any entity of interest, such as, but not limited to, a human entity, an automated component, a device, an item, an animal, etc.

Typically, the magnitude of the reflections 212 depend on the size of the object 210, the color of the object 210 and the distance of the object 210 from the IR sensor 204. As an example, a white shirt can produce higher reflections than a black shirt. In addition to the reflections 212 from the object 210, the sensor 204 can receive various other signals 214, such as, but not limited to, electrical crosstalk, optical crosstalk and/or environmental backscatter. Each of these signals represents interference to the detection of the object of interest. Of these interferences, electrical and optical crosstalk can be approximated to be relatively constant through the life time of the device, and can be calibrated at the manufacturing or development stage of the application. Environmental backscatter 214 can be received from various sources in the optical field of the sensor 204, and can include most any signal that is not of interest to the detection of the object 210. For example, objects such as a desk surface, a couch, a television display, a soda can, etc., are not useful targets, but are detected as a significant component of the signal received at the sensor 204. In one embodiment, sensor front end 108 can process the signal from sensor 204 to ignore the environmental backscatter signals and isolates the signals 212 from the object 210 to identify the proximity of the object 210 from the sensor 204.

According to an aspect, system 200 utilizes Time-of-Flight (TOF) measurements, which rely on the finite speed of light. The finite speed causes a delay between the projection of an electromagnetic wave and its reflection from an object, which is proportional to the distance of the object. In system 200, the distance can be measured as a phase delay of a modulated (e.g., at 5 MHz) IR LED signal. Moreover, the phase delay of the signal received at the sensor front end 108 includes phase errors introduced by phase delays contributed by various components in the signal path. To account for these errors, calibration component 216 can be utilized. During calibration, the input between the sensor 204 and sensor front end 108 is disconnected and an output from the attenuation component 106 is provided to the sensor front end 108. Moreover, the driver sensing component 104 senses the voltage or current at the LED. An attenuated version of the driver sensed signal is provided to the sensor front end 108, wherein, the phase delay of the signal path is measured, such that it can be removed from future measurements. After calibration, the connection between the sensor 204 and sensor front end 108 is restored and the connection between the attenuation component 106 and sensor front end 108 is disconnected. Typically, the calibration can be performed at most any time, such as, but not limited to, during set-up/initialization, during normal operation, during power-up, periodically, automatically, or when requested by the user. Additionally or alternately, the calibration can also be performed during product testing.

It can be appreciated that the mechanical design of system 200 can include different component selections, component placement, dimensions, glass cover characteristics, LED selections, isolation techniques between sensor 204 and LED 202, etc., to achieve an optimal proximity sensing. Further, it can be appreciated that the LED driver 206, driver sensing component 104, attenuation component 106, and the sensor front end 108, can include most any electrical circuit(s) that can include components and circuitry elements of any suitable value in order to implement the embodiments of the subject innovation. Furthermore, various IR bands can be employed in system 200 (e.g., Near IR, Mid-Wave IR and Long-Wave IR). Each band can have unique LEDs and Sensors. Oftentimes, some visible detector systems can work in the Near IR band and can include the detector integrated into the system IC. In addition, it can be appreciated that system 200 is not limited to utilizing IR light, and LEDs/sensors/detectors can utilize signals of most any wavelength.

Figure 3:
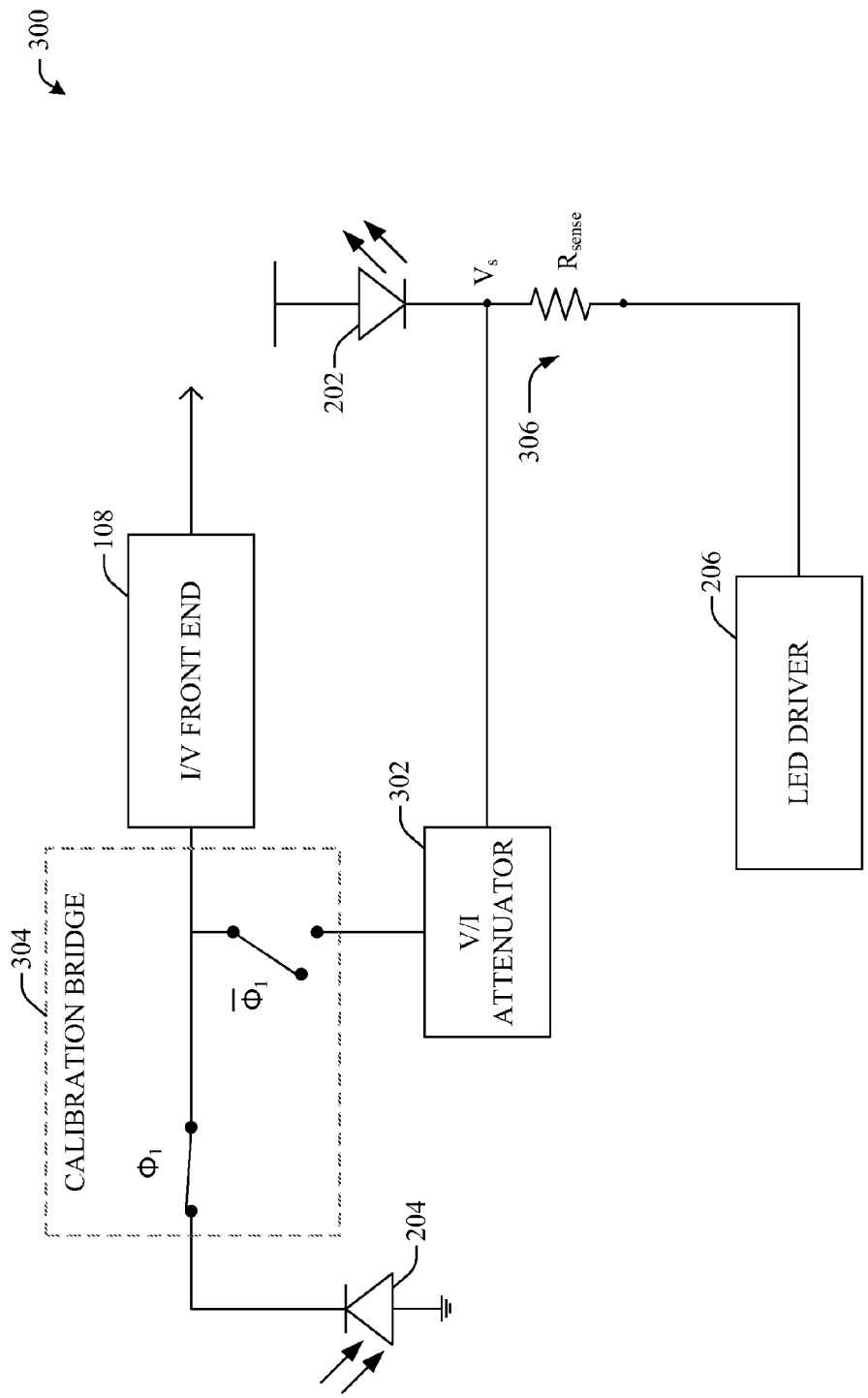
FIG. 3 illustrates an exemplary circuit diagram that employs an automatic zero calibration technique for a Time-of-Flight (TOF) transceiver that senses voltage at a light emitting diode (LED).

FIG. 3 illustrates an example circuit diagram 300 that provides automatic zero phase calibration for TOF transceivers by sensing voltage at an LED in accordance with an aspect of the subject innovation. Typically, TOF transceivers can facilitate proximity/motion detection by transmitting a light signal, and identifying the phase delay of a light signal reflected from an object. To accurately calculate the phase delay, the transceiver can utilize circuit 300. Moreover, phase errors, added in the signal path, are detected and calibrated to accurately and correctly identify zero phase. It can be appreciated that LED 202, sensor 204, LED driver 206, and front end 108 can include functionality as described in detail with respect to systems 100 and 200.

According to an aspect, the voltage at node $V_s$ is sensed and provided to attenuator 302. In one example, attenuator 302 can be most any V/I attenuator that includes most any passive device that weakens or attenuates the sensed voltage. The attenuator 302 can provide a fixed and/or adjustable amount of attenuation and also provide isolation between the front end 108 and the LED driver 206. Further, circuit 300 includes a calibration bridge 304 that can switch/toggle between normal operation and calibration modes. During the normal operation mode, $\phi_1$ is high and the front end 108 receives the signal from the photodiode 204. Moreover, the front end 108 calculates phase delay to identify distance/presence of an object in the sense field. During calibration mode, $\phi_1$ is low and a signal from the attenuator 302 is provided to the front end 108. It can be appreciated that most any circuit can be utilized to provide an attenuated version of the sensed current to the front end 108. In one example, the output of the LED driver can be lowered/decreased and the voltage at node $V_s$ can be directly provided to the front end 108 during the calibration mode (e.g., instead of employing an attenuator). Specifically, the signal is an attenuated version of the LED voltage, which is indicative of phase errors in the signal path. Typically, the phase errors can be introduced by including, but not limited to, analog front end, DSP, LED driver, board parasitic, package parasitic, etc. In one aspect, the front end 108 utilizes the signal from the attenuator 302 to measure the phase delay of the system, which can be removed from future measurements. For example, when $\phi_1$ is high and signal is received from the sensor 204, the front end 108 computes the phase delay of the received signal accurately by compensating for the phase delay of the system (e.g., determined during the calibration mode).

In one example, the calibration bridge 304 can have a trimmable phase delay, which can be set to substantially set to zero during manufacturing. Typically, the calibration bridge 304 can be constructed from simple elements, such as, but not limited to two one-way SPST (Single pole, single throw) switches or a two-way SPDT (Single pole, double throw) switch (not shown), which are not subject to significant drift over unit lifetime. Moreover, the calibration bridge 304 can serve an effective means to remove drift of the more sensitive amplifier(s), filter(s), modulator(s) and/or demodulator(s) within the main signal path. In one embodiment, the calibration bridge 304 can be switched periodically, at a preset time, on power up or on demand. Accordingly, the value for $\phi_1$ can be toggled and an appropriate mode of operation can be selected.

Figure 4:
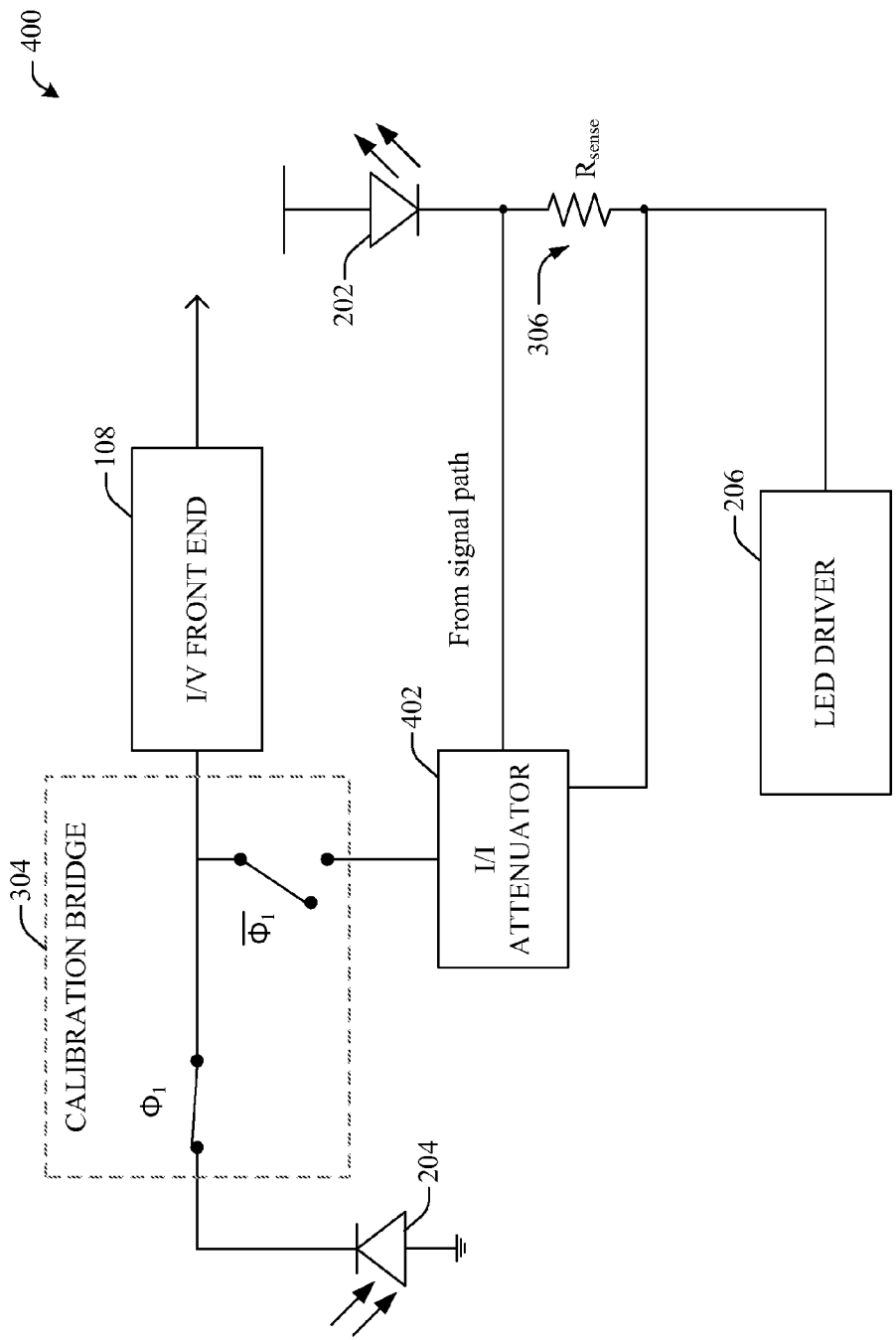
FIG. 4 illustrates an exemplary circuit diagram that employs an automatic zero calibration technique for a Time-of-Flight (TOF) transceiver that senses current at a light emitting diode (LED).

Referring to FIG. 4, there illustrated is an example circuit 400 for automatic phase delay calibration in accordance with an aspect of the disclosed specification. It can be appreciated that the LED 202, sensor 204, LED driver 206, front end 108, and calibration bridge 304 can include functionality as described in detail with respect to systems 100, 200, and 300. In this example circuit, the current across resistor $R_{sense}$ 306 is sensed and provided to the I/I attenuator 402. It can be appreciated that the subject disclosure is not limited to sensing voltage at or current across $R_{sense}$ 306 and that voltage and/or current can be sensed from any point in the signal path (as shown by the dotted line). In one aspect, the attenuator 402 reduces the power and/or amplitude of the sensed signal and provides it to the front end 108 during calibration mode (when $\phi_1$ is low). As noted above, it can be appreciated that the LED driver output can be reduced during calibration and the current through $R_{sense}$ 306 can be directly provided to the front end 108. Moreover, during the calibration mode, the front end 108 can identify the phase delay introduced by the system, which provide errors in distance calculation. In addition, the phase delay can be utilized to accurately identify distance, during the normal mode.

Figure 5:
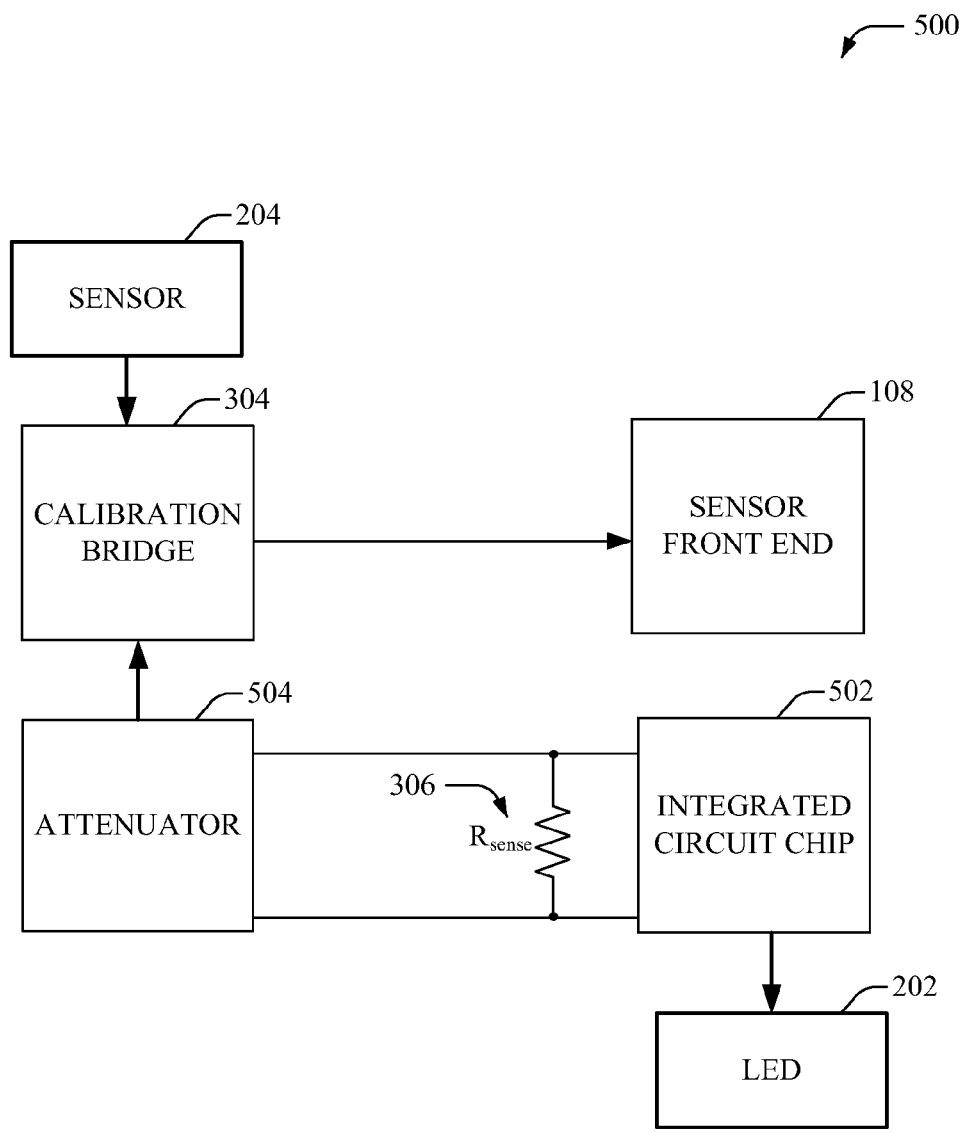
FIG. 5 illustrates an example system that facilitates automatic zero calibration in a TOF detector.

Referring now to FIG. 5, there illustrated is an example system 500 that facilitates automatic phase calibration in a TOF detector. In one aspect, system 500 can include an IC chip 502, for example, that includes the LED driver. The IC 502 can comprise one or more sense pins that provide input to a signal attenuator 504. Although the sensor front end 108 is depicted external to the IC 502, it can be appreciated that the sensor front end 108 can be included within IC 502.

In one example, resistor $R_{sense}$ 306 can be externally connected at the LED and can provide a signal (e.g., current or voltage) to the attenuator 504. Based on the mode of operation, for example, calibration mode or normal operation mode, the calibration bridge 304 can provide an appropriate input to the sensor front end 108. In one example, during the calibration mode, the calibration bridge 304 provides the attenuated driver sensed signal to the sensor front end 108. Alternately, in the normal operation mode, a signal from the sensor 204 is provided to the sensor front end 108. Since the resistor $R_{sense}$ 306, attenuator 504, and/or calibration bridge 304 are external to IC 502, board and/or package parasitics can be accounted for during calibration. In an alternate embodiment, the resistor $R_{sense}$ 306, attenuator 504, and/or calibration bridge 304 can reside within IC 502 (not shown).

Figure 6:
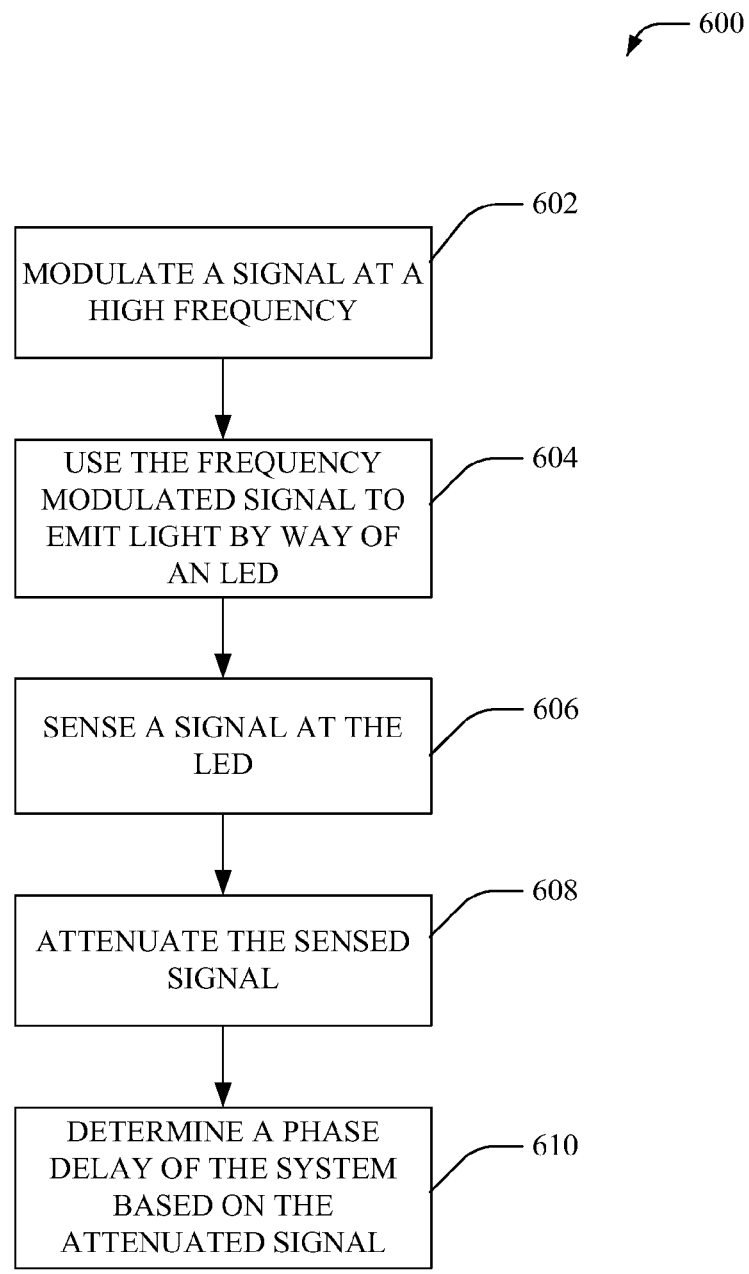
FIG. 6 illustrates an exemplary methodology that can automatically discern an error introduced by a TOF system, during distance measurement.
Figure 7:
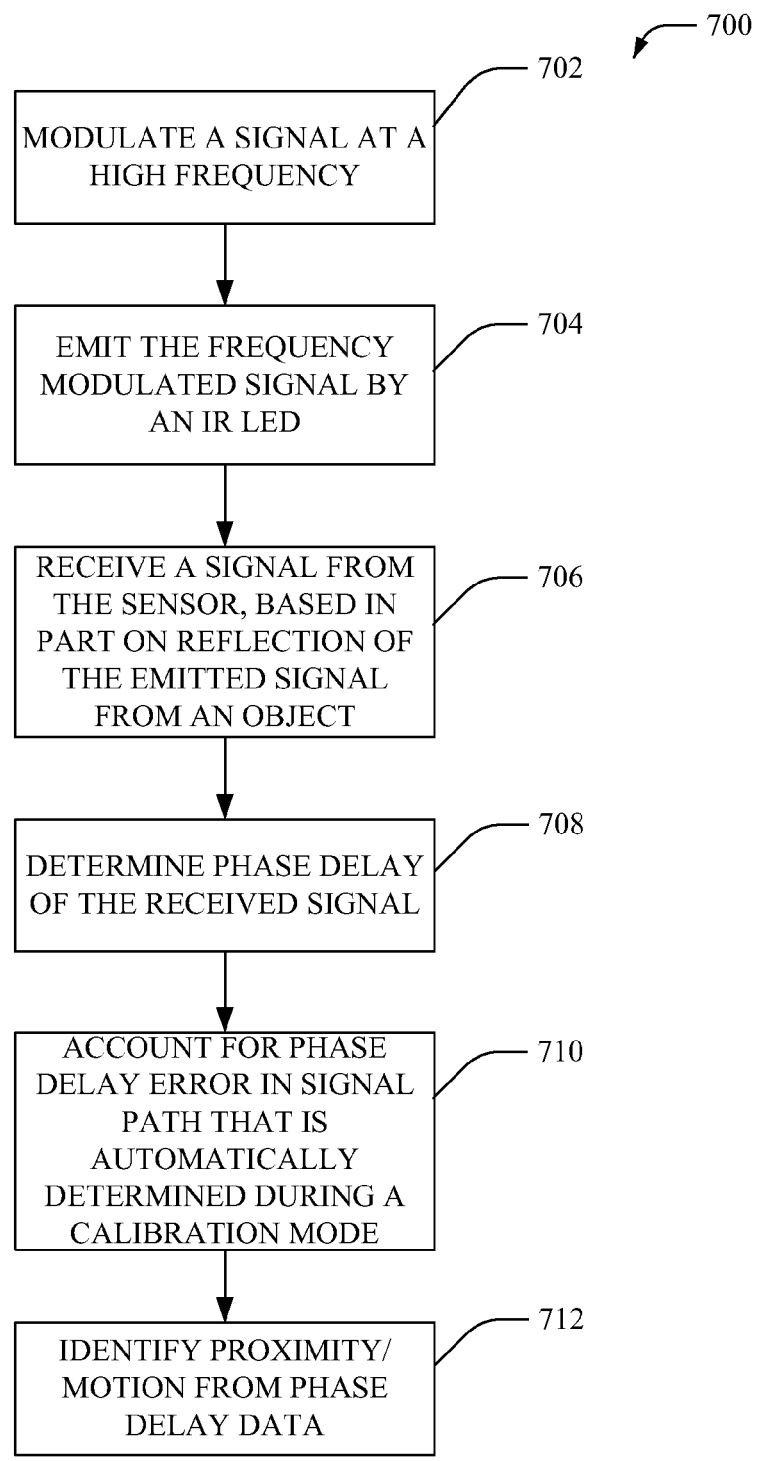
FIG. 7 illustrates an exemplary methodology for accurately measuring distance between an object and a sensor in accordance with an aspect of the subject specification.

FIGS. 6-7 illustrate a methodology and/or flow diagram in accordance with the disclosed subject matter. For simplicity of explanation, the methodologies are depicted and described as a series of acts. It is to be understood and appreciated that the subject innovation is not limited by the acts illustrated and/or by the order of acts, for example acts can occur in various orders and/or concurrently, and with other acts not presented and described herein. Furthermore, not all illustrated acts may be required to implement the methodologies in accordance with the disclosed subject matter. In addition, those skilled in the art will understand and appreciate that the methodologies could alternatively be represented as a series of interrelated states via a state diagram or events. Additionally, it should be further appreciated that the methodologies disclosed hereinafter and throughout this specification are capable of being stored on an article of manufacture to facilitate transporting and transferring such methodologies to computers. The term article of manufacture, as used herein, is intended to encompass a computer program accessible from any computer-readable device or computer-readable storage/communications media.

FIG. 6 illustrates an example methodology 600 that can automatically discern an error introduced by a TOF system, during distance measurement. Typically, methodology 600 can be employed by TOF systems utilized in various applications, such as, but not limited to consumer electronic devices (e.g., cell phones, laptops, media players, gaming systems, night-vision systems, televisions, copiers, printers, cameras, etc.), mechanical systems (e.g., door/window mechanism), industrial automation systems, robotics, medical systems, etc.

At 602, a signal, for example, input to a LED, can be modulated at a high frequency (e.g., 1 MHz-50 MHz). As an example, most any frequency modulation technique can be employed for modulation. At 604, the modulated signal can be emitted by the LED (e.g., IR LED). Typically, the range of the LED can be selected based on the application (e.g., 1-2 meters). According to an aspect, at 606, the signal at the LED (e.g., voltage or current) can be sensed. At 608, the sensed signal can be attenuated. Further at 610, a phase delay introduced by the system can be identified based in part on the attenuated signal. This phase delay can include phase errors introduced by various elements in the signal path as well as board and/or package parasitics, and can be appropriately calibrated out. Typically, the system phase delay is utilized during "normal operation" to accurately measure distance and compensate for phase delay errors introduced in the signal path. In one example, methodology 600 can be initiated at most any time, such as, but not limited to, a specified time, periodically and/or dynamically.

Referring now to FIG. 7, there illustrated is an example methodology 700 for accurately measuring distance between an object and a sensor in accordance with an aspect of the subject specification. Methodology 700 can employ the TOF principle for identifying the distance based on a time or phase delay of a modulated signal between a transmitter and a receiver. Moreover, the delay is proportional to the distance travelled by the modulated signal. However, an error can be introduced in the delay by various elements, such as, but not limited to, circuits, board/package parasitics, etc. In one aspect, this error can be automatically measured and calibrated out during a calibration mode, by sensing a signal at a transmitter.

At 702, a signal that drives a transmitter (e.g., IR LED), can be modulated at a high frequency (e.g., 1 MHz-50 MHz). As an example, most any frequency modulation technique can be employed for modulation. At 704, the modulated signal can be emitted by the IR LED. The emitted IR signal reflects off of various objects (moving and/or stationary) within the optical field and the reflected signal is received at an IR sensor. Moreover, the IR sensor generates an electrical signal indicative of the amount of light incident on the sensor. At 706, the signal is received from the sensor based in part on reflections of the emitted signal from an object. Further, at 708, a phase delay of the received signal can be determined. In addition, at 710, the phase delay error in the signal path that is automatically determined during the calibration mode is accounted for, for example, by correcting the phase delay of the received signal. In one example, the phase delay error can be subtracted from the phase delay of the received signal. At 712, proximity and/or motion of the object can be accurately identified based on the phase delay data.

Figure 8:
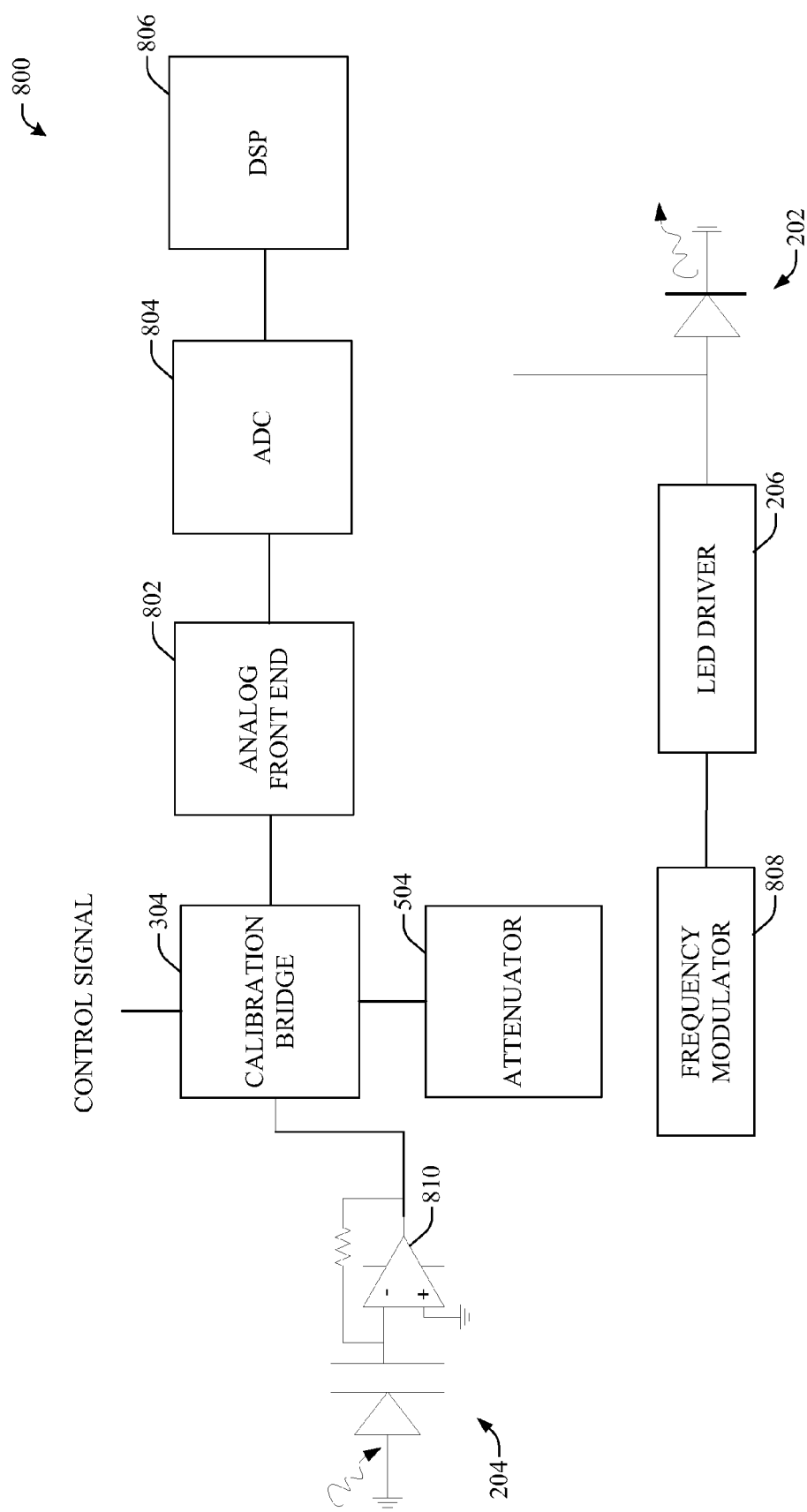
FIG. 8 illustrates an exemplary functional block diagram for the architecture of the subject innovation.

In order to provide additional context for various aspects of the subject specification, FIG. 8 illustrates an exemplary functional block diagram for the architecture 800 of the subject innovation. In one aspect, the systems (e.g., 100-500) disclosed herein can be employed in a long range reflection based proximity and motion detector depicted in FIG. 8. The architecture 800 includes a LED 202 and associated driver circuitry 206 and a frequency modulator 808 that modulates the signal input to the LED, a photodiode sensor 204, an analog front end and signal processing 802, data conversion circuitry 804, digital control and signal processing 806, interface circuitry and results display (not shown for simplicity).

According to an aspect of the subject innovation, the architecture 800 can include a Trans-Inductance Amplifier (TIA) 810 (and/or a Trans-Inductance resistor (TIR) and/or other photo diode devices) that amplifies the signal from the sensor 204. Moreover the output of the TIA 810 can be connected to the calibration bridge 304, which in turn connects the output of the TIA 810 to an analog Front End (FE) 802, during a normal operation mode. The output of the Front End 802 is subjected to multiple stages of voltage gain to maximize the SNR of the output signal. In one example, the voltage gain is adaptively set based on the magnitude of the signal received from the Front End 802, which is potentially made up of both measureable interferers such as a backscatter and a crosstalk from the LED, and also the desired signal to be measured. The interferers are dynamically calibrated out of the measurement to improve the sensitivity, during a calibration mode. According to an aspect, the attenuator 504 provides an attenuated version of a signal sensed at the LED 202, which is then provided to the analog front end 802 by the calibration bride 304, during the calibration mode. Moreover, the control signal switches the calibration bridge between operation modes.

The architecture 800 also includes a Demodulator (not shown for simplicity) with low pass filters (LPFs), Analog to Digital Converters (ADCs) 804, a Universal Serial Bus (USB) processor for a Control Interface, and a digital signal processor (DSP) 806 that can include a Computer Programmable Logic Device (CPLD) comprising several modules. Moreover, the DSP 806 can process the digital signal to measure proximity of an object, motion of an object, presence of an object and/or ambient light within a sense field of the sensor 302

The architecture 800 of the subject innovation can be used in many applications including computers, automotive, industrial, television displays and others. For example, the architecture 800 can be used to detect that a user has entered the room and automatically cause a laptop computer in hibernation mode to wake up and enter into the active mode so that the user can use it. In another example, the architecture 800 of the subject innovation can be used to automatically and adaptively adjust the intensity of a liquid crystal display (LCD) based on the ambient lighting conditions. According to an aspect of the subject innovation, the architecture 800 can perform motion and proximity sensing at a range of up to 1-2 meters. According to another aspect of the subject innovation, the architecture 800 of the subject innovation can perform its operations by using less than twenty milli-watts (mW) of power.

What has been described above includes examples of the subject innovation. It is, of course, not possible to describe every conceivable combination of components or methodologies for purposes of describing the claimed subject matter, but one of ordinary skill in the art may recognize that many further combinations and permutations of the subject innovation are possible. Accordingly, the claimed subject matter is intended to embrace all such alterations, modifications, and variations that fall within the spirit and scope of the appended claims.

In particular and in regard to the various functions performed by the above described components, devices, circuits, systems and the like, the terms (including a reference to a "means") used to describe such components are intended to correspond, unless otherwise indicated, to any component which performs the specified function of the described component (e.g., a functional equivalent), even though not structurally equivalent to the disclosed structure, which performs the function in the herein illustrated exemplary aspects of the claimed subject matter. In this regard, it will also be recognized that the innovation includes a system as well as a computer-readable medium having computer-executable instructions for performing the acts and/or events of the various methods of the claimed subject matter.

The aforementioned systems/circuits/modules have been described with respect to interaction between several components. It can be appreciated that such systems/circuits/modules and components can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it should be noted that one or more components may be combined into a single component providing aggregate functionality or divided into several separate sub-components, and any one or more middle layers, such as a management layer, may be provided to communicatively couple to such sub-components in order to provide integrated functionality. Any components described herein may also interact with one or more other components not specifically described herein but generally known by those of skill in the art.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

What is claimed is:

1. A method for use in calibrating a system that includes
    a driver configured to produce a drive signal that can be used to drive a light emitting element with the drive signal to thereby cause a light signal to be emitted,
    an optical sensor configured to produce a sensor signal that is indicative of a portion of the light signal that reflects from one or more objects and is incident on the optical sensor, and
    circuitry configured to produce at least one of a time and phase delay measurement based on a sensor signal produced by the optical sensor, wherein the at least one of the time and phase delay measurement can be used to determine at least one of a distance and presence of one or more objects relative to the optical sensor;
    the method comprising:
    (a) during a calibration mode,
    (a.1) using the driver to produce a drive signal;
    (a.2) providing a version of the drive signal to the circuitry configured to produce the at least one of the time and phase delay measurement; and
    (a.3) using the circuitry configured to produce the at least one of the time and phase delay measurement to determine the at least one of the time and phase delay introduced by the system; and
    (b) during an operational mode, using the at least one of the time and phase delay introduced by the system, as determined during the calibration mode, to calibrate at least one of an actual time and phase delay measurement that is made by the circuitry configured to produce at least one of the time and phase delay measurement.

2. The method of claim 1, wherein step (b) includes, during the operational mode:
    (b.1) using the driver to produce a drive signal that drives a light emitting element to thereby cause a light signal to be emitted;
    (b.2) using the optical sensor to produce a sensor signal that is indicative of a portion of the light signal that reflects from one or more objects and is incident on the optical sensor;
    (b.3) producing the at least one of the actual time and phase delay measurement based on the sensor signal; and (b.4) using the at least one of the time and phase delay introduced by the system, as determined at step (a.3), to calibrate the at least one of the actual time and phase delay measurement produced at step (b.3).

3. The method of claim 2, wherein step (b.4) comprises correcting the at least one of the actual time and phase delay measurement produced at step (b.3) to account for the at least one of the time and phase delay introduced by the system as determined at step (a.3).

4. The method of claim 2, wherein step (b.4) comprises subtracting the at least one of the time and phase delay introduced by the system, as determined at step (a.3), from the at least one of the actual time and phase delay measurement produced at step (b.3).

5. The method of claim 1, wherein:
step (a.1) includes using the driver to produce a drive signal having a same power and amplitude as is produced during the operational mode; and
step (a.2) includes attenuating the drive signal produced by the driver, or a sensed version thereof, to thereby produce an attenuated version of the drive signal, and providing the attenuated version of the drive signal to the circuitry configured to produce the at least one of the time and phase delay measurement.

6. The method of claim 1, wherein:
step (a.1) includes using the driver to produce a drive signal having a reduced at least one of power and amplitude compared to a drive signal produced during the operational mode; and
step (a.2) includes providing the drive signal having the reduced at least one of power and amplitude, or a sensed version thereof, to the circuitry configured to produce the at least one of the time and/or and phase delay measurement.

7. The method of claim 1, wherein the circuitry configured to produce the at least one of the time and phase delay measurement includes front end circuitry.

8. The method of claim 7, wherein the front end circuitry includes one or more amplifiers, one or more filters, and one or more demodulators, each of which can cause a delay that can contribute to the at least one of the time and phase delay introduced by the system.

9. The method of claim 7, wherein the circuitry configured to produce the at least one of the time and phase delay measurement also includes an analog-to-digital converter (ADC) and a digital signal processor (DSP).

10. The method of claim 1, further comprising:
(c) detecting the at least one of the distance and presence of one or more objects relative to the optical sensor based on the calibrated at least one of the time and phase delay measurement.

11. A system, comprising:
a driver configured to produce a drive signal that can be used to drive a light emitting element to thereby cause a light signal to be emitted;
an optical sensor configured to produce a sensor signal that is indicative of a portion of the light signal that reflects from one or more objects and is incident on the optical sensor; and
circuitry configured to produce at least one of a time and phase delay measurement based on the sensor signal produced by the optical sensor, wherein the at least one of the time and phase delay measurement can be used to determine at least one of a distance and presence of one or more objects relative to the optical sensor;
wherein the system can operate in a calibration mode and an operational mode;

wherein during the calibration mode,
the driver produces a drive signal;
the circuitry configured to produce the at least one of the time and phase delay measurement receives a version of the drive signal, and based thereon, determines the at least one of the time and phase delay introduced by the system; and
wherein during the operational mode,
the circuitry configured to produce the at least one of the time and phase delay measurement uses the at least one of the time and phase delay introduced by the system, as determined during the calibration mode, to calibrate at least one of an actual time and phase delay measurement that is made by the circuitry.

12. The system of claim 11, wherein during the operational mode:
the driver produces a drive signal that drives a light emitting element to thereby cause a light signal to be emitted;
the optical sensor produces the sensor signal that is indicative of a portion of the light signal that reflects from one or more objects and is incident on the optical sensor; and
the circuitry configured to produce the at least one of the time and phase delay measurement produces the at least one of the actual time and phase delay measurement based on the sensor signal, and calibrates the at least one of the actual time and phase delay measurement based on the at least one of the time and phase delay introduced by the system, as determined during the calibration mode.

13. The system of claim 12, wherein during the operational mode:
the circuitry configured to produce the at least one of the time and phase delay measurement calibrates the at least one of the actual time and phase delay measurement by correcting the at least one of the actual time and phase delay measurement to account for the at least one of the time and phase delay introduced by the system, as determined during the calibration mode.

14. The system of claim 12, wherein during the operational mode:
the circuitry configured to produce the at least one of the time and phase delay measurement calibrates the at least one of the actual time and phase delay measurement by subtracting the at least one of a time and/or and phase delay introduced by the system, as determined during the calibration mode, from the at least one of the actual time and phase delay measurement.

15. The system of claim 11, further comprising:
an attenuator;
wherein during the calibration mode
the drive signal produced by the driver has a same power and amplitude as is produced during the operational mode; and
the attenuator attenuates the drive signal produced by the driver, or a sensed version thereof, to thereby produce an attenuated version of the drive signal that is provided to the circuitry configured to produce the at least one of the time and phase delay measurement.

16. The system of claim 11, wherein during the calibration mode:
the drive signal produced by the driver has a reduced at least one of power and amplitude compared to the drive signal produced during the operational mode; and
the drive signal having the reduced at least one of power and amplitude, or a sensed version thereof, is provided to the circuitry configured to produce the at least one of the time and phase delay measurement.

17. The system of claim 11, wherein the circuitry configured to produce the at least one of the time and phase delay measurement includes front end circuitry.

18. The system of claim 17, wherein the front end circuitry includes one or more amplifiers, one or more filters, and one or more demodulators, each of which can cause a delay that can contribute to the at least one of the time and phase delay introduced by the system.

19. The system of claim 17, wherein the circuitry configured to produce the at least one of the time and phase delay measurement also includes an analog-to-digital converter (ADC) and a digital signal processor (DSP).

20. The system of claim 19, wherein, during the operational mode, the DSP is configured to detect the at least one of the distance and presence of one or more objects relative to the optical sensor based on at least one of a calibrated time and phase delay measurement.

* * * * *

UNITED STATES PATENT AND TRADEMARK OFFICE
CERTIFICATE OF CORRECTION

PATENT NO. : 8,274,037 B2
APPLICATION NO. : 13/013173
DATED : September 25, 2012
INVENTOR(S) : D. Ritter et al.

It is certified that error appears in the above-identified patent and that said Letters Patent is hereby corrected as shown below:

Column 11, line 33 (claim 6, line 9), please omit "and/or".

Column 12, line 46 (claim 14, line 6), please omit "and/or".

Signed and Sealed this
Twenty-sixth Day of March, 2013

Teresa Stanek Rea
*Acting Director of the United States Patent and Trademark Office*